US005916597A

United States Patent [19]
Lee et al.

[11] Patent Number: 5,916,597
[45] Date of Patent: Jun. 29, 1999

[54] COMPOSITION AND METHOD USING SOLID-PHASE PARTICLES FOR SUSTAINED IN VIVO RELEASE OF A BIOLOGICALLY ACTIVE AGENT

[75] Inventors: Hye-Jung Lee; OluFunmi L. Johnson, both of Cambridge; Stephen E. Zale, Hopkington; Mark A. Tracy, Arlington, all of Mass.

[73] Assignee: Alkermes Controlled Therapeutics, Inc., Cambridge, Mass.

[21] Appl. No.: 08/705,197

[22] Filed: Aug. 29, 1996

Related U.S. Application Data

[60] Provisional application No. 60/003,006, Aug. 31, 1995.
[51] Int. Cl.⁶ .................................. A61K 9/16; A61K 9/52
[52] U.S. Cl. ............................................................ 424/501
[58] Field of Search ................................... 424/489, 459, 424/501

[56] References Cited

U.S. PATENT DOCUMENTS

| 3,523,906 | 8/1970 | Vrancken et al. | 252/316 |
|---|---|---|---|
| 3,691,090 | 9/1972 | Kitajima et al. | 252/316 |

(List continued on next page.)

FOREIGN PATENT DOCUMENTS

| 0 123 291 A2 | 10/1984 | European Pat. Off. . |
|---|---|---|
| 0 251 680 A2 | 1/1988 | European Pat. Off. . |
| 0266119A3 | 5/1988 | European Pat. Off. . |
| 0 281 299 A1 | 9/1988 | European Pat. Off. . |
| 0 307 097 A2 | 3/1989 | European Pat. Off. . |
| 0330180A1 | 8/1989 | European Pat. Off. . |
| 0537559A1 | 4/1993 | European Pat. Off. . |
| 0580 428A1 | 1/1994 | European Pat. Off. . |
| 0 595 030 A2 | 5/1994 | European Pat. Off. . |
| 0633 020A1 | 1/1995 | European Pat. Off. . |
| 89/03678 | 5/1989 | WIPO . |
| 90/09166 | 8/1990 | WIPO . |
| 90/13285 | 11/1990 | WIPO . |
| 90/13780 | 11/1990 | WIPO . |
| 91/12882 | 9/1991 | WIPO . |
| 91/18927A1 | 12/1991 | WIPO . |
| 92/11844 | 7/1992 | WIPO . |
| 92/19226 | 11/1992 | WIPO . |
| 93/02712 | 2/1993 | WIPO . |
| 93/07861 | 4/1993 | WIPO . |
| 93/17668 | 9/1993 | WIPO . |
| 93/25221 | 12/1993 | WIPO . |
| 94/07469 | 4/1994 | WIPO . |
| 94/12158 | 6/1994 | WIPO . |
| 94/19373A1 | 9/1994 | WIPO . |
| 95/11010 | 4/1995 | WIPO . |
| WO95/29664 A1 | 11/1995 | WIPO . |
| 96/07399 A1 | 3/1996 | WIPO . |

OTHER PUBLICATIONS

Pratt, L., et al., "The Effect of Ionic Electrolytes on Hydrolytic Degradation of Biodegradable Polymers: Mechanical and Thermodynamic Properties and Molecular Modeling," *J. Polymer Science* 31(7): 1759–1769 (1993).

(List continued on next page.)

*Primary Examiner*—Peter F. Kulkosky
*Attorney, Agent, or Firm*—Hamilton, Brook, Smith & Reynolds, P.C.

[57] ABSTRACT

Composition for the sustained release of a biologically active agent in vivo. The composition comprises microcarriers containing a first solid-phase biocompatible material and a biologically active agent, wherein said microcarriers sustain the in vivo release of the biologically active agent. The composition also contains particles of a second biocompatible solid-phase material wherein the second solid-phase material further sustains the in vivo release of the biologically active agent.

The invention also relates to a method for sustaining effective serum levels of a biologically active agent in a subject, including forming an injectable dose containing an effective amount of a biologically active agent, wherein the agent is contained in a microcarrier, with a release-period sustaining amount of a solid-phase material. The method further includes administering the injectable dose to the subject.

18 Claims, 6 Drawing Sheets

U.S. PATENT DOCUMENTS

| | | | |
|---|---|---|---|
| 3,737,337 | 6/1973 | Schnoring et al. | 117/100 |
| 3,887,699 | 6/1975 | Yolles | 424/19 |
| 3,891,570 | 6/1975 | Fukushima et al. | 252/316 |
| 3,928,566 | 12/1975 | Briggs et al. | 424/94 |
| 4,166,800 | 9/1979 | Fong | 252/316 |
| 4,235,236 | 11/1980 | Theeuwes | 128/260 |
| 4,237,114 | 12/1980 | Cardarelli | 424/78 |
| 4,252,791 | 2/1981 | Grossberg et al. | 424/85 |
| 4,389,330 | 6/1983 | Tice et al. | 427/213.36 |
| 4,391,797 | 7/1983 | Folkman et al. | 424/19 |
| 4,530,840 | 7/1985 | Tice et al. | 514/179 |
| 4,530,901 | 7/1985 | Weissmann | 435/70 |
| 4,542,025 | 9/1985 | Tice et al. | 424/78 |
| 4,637,905 | 1/1987 | Gardner | 264/4.3 |
| 4,655,777 | 4/1987 | Dunn et al. | 623/16 |
| 4,675,189 | 6/1987 | Kent et al. | 424/490 |
| 4,711,782 | 12/1987 | Okada et al. | 424/455 |
| 4,732,889 | 3/1988 | Cynshi et al. | 514/8 |
| 4,767,628 | 8/1988 | Hutchinson | 424/426 |
| 4,806,524 | 2/1989 | Kawaguchi et al. | 514/8 |
| 4,835,139 | 5/1989 | Tice et al. | 514/15 |
| 4,853,218 | 8/1989 | Yim et al. | 424/85.7 |
| 4,871,538 | 10/1989 | Yim et al. | 424/85.7 |
| 4,879,272 | 11/1989 | Shimoda et al. | 514/8 |
| 4,891,225 | 1/1990 | Langer et al. | 424/428 |
| 4,897,268 | 1/1990 | Tice et al. | 424/422 |
| 4,906,474 | 3/1990 | Langer et al. | 424/428 |
| 4,962,091 | 10/1990 | Eppstein et al. | 514/2 |
| 4,981,696 | 1/1991 | Loomis et al. | 424/486 |
| 4,992,419 | 2/1991 | Woog et al. | 514/8 |
| 5,019,400 | 5/1991 | Gombotz et al. | 424/497 |
| 5,075,115 | 12/1991 | Brine | 424/486 |
| 5,122,367 | 6/1992 | Ron et al. | 424/80 |
| 5,126,147 | 6/1992 | Silvestri et al. | 424/497 |
| 5,145,674 | 9/1992 | Lane et al. | 424/78.08 |
| 5,176,907 | 1/1993 | Leong | 424/78.08 |
| 5,192,741 | 3/1993 | Orsolini et al. | 514/4 |
| 5,344,654 | 9/1994 | Rueger et al. | 424/423 |
| 5,413,797 | 5/1995 | Khan et al. | 424/489 |
| 5,441,734 | 8/1995 | Reichert et al. | 424/85.7 |
| 5,603,961 | 2/1997 | Suzuki et al. | 424/489 |
| B1 4,985,404 | 4/1992 | Mitchell. | |

OTHER PUBLICATIONS

Costantino, H. R., et al., "Solid–Phase Aggregation of Proteins under Pharmaceutically Relevant Conditions," *J. of Pharmaceutical Sciences*, 83(12): 1662–1669 (1994).

Costantino, H. R., et al., "Moisture–Induced Aggregation of Lyophilized Insulin," *Pharmaceutical Research*, 11(1): 21–29 (1994).

Costantino, H. R., et al., "Aggregation of a Lyophilized Pharmaceutical Protein, Recombinant Human Albumin: Effect of Moisture and Stabilization by Excipients," *Biotechnology*, 13: 493–496 (1995).

Creighton, T. E., "Physical Forces That Determine the Properties of Proteins." *In Proteins, Structures and Molecular Principles*, (NY: W. H. Freeman and Company), pp. 149–150.

Cunningham, B. C., et al., "Dimerization of Human Growth Hormone by Zinc," *Science*, 253: 545–548 (Aug. 1991).

Sato, Toyomi, et al., "Porous Biodegradable Microspheres for Controlled Drug Delivery. I. Assessment of Processing Conditions and Solvent Removal Techniques," *Pharmaceutical Research*, 5(1): 21–29 (1988).

Langer, R., "New Methods of Drug Delivery," *Science*, 249: 1527–1533 (Sep. 1990).

Liu, W. R., et al., "Moisture–Induced Aggregation of Lyophilized Proteins in the Solid State," *Biotechnology and Bioengineering*, 37: 177–184 (1991).

Lu, W., and Park, T. G., "Protein Release from Poly(lactic-co–glycolic acid) Microspheres: Protein Stability Problems," *PDA J. of Pharmaceutical Science & Technology*, 49(1): 13–19 (Jan.–Feb. 1995).

Cohen, S., et al., "Controlled Delivery Systems for Proteins Based on Poly(Lactic/Glycolic Acid) Microspheres," *Pharmaceutical Research*, 8(6): 713–720 (1991).

Hora, M. S., et al., "Release of Human Serum Albumin from Poly(lactide–co–glycolide) Microspheres," *Pharmaceutical Research*, 7(11): 1190–1194 (1990).

Hageman, M. J., et al., "Preformulation Studies Oriented Toward Sustained Delivery of Recombinant Somatotropins," *J. Agric. Food Chem.*, 40: 348–355 (1992).

Cleland, J. L., et al., "Characterization of Recombinant Human Growth Hormone–PLGA Formulations in Animals," *Proceed, Intern. Symp. Control. Rel. Bioact. Mater.*, 22: 143–144 (1995).

Cleland, J. L., et al., "One Month Continuous Release Recombinant Human Growth Hormone–PLGA Formulations," *Proceed. Intern. Symp. Control. Rel. Bioact. Mater.*, 22: 149–150 (1995).

Mullerad, J., et al., "Delivery of IL–1 Microspheres to Tumor Macrophages," *Proceed. Intern. Symp. Control. Rel. Bioact. Mater.*, 22: 512–513 (1995).

Cleland, J. L., et al., "In Vitro Release of Bioactive Recombinant Human Interferon–γ From PLGA Microspheres," *Proceed. Intern. Symp. Control. Rel. Bioact. Mater.*, 22: 518–519 (1995).

Park, T. G., et al., "Importance of In Vitro Experimental Conditions on Protein Release Kinetics, Stability and Polymer Degradation in Protein Encapsulated Poly(D,:–Lactic Acid–Co–Glycolic Acid) Microspheres," *J. of Controlled Release*, 33: 211–222 (1995).

Nagata, S., et al., "Synthesis in *E. Coli* of a Polypeptide with Human Leukocyte Interferon Activity," *Nature*, 284: 316–320 (Mar. 1980).

Rubinstein, M., "The Structure of Human Interferons." *Biochimica et Biophysica Acta.*, 695: 5–16 (1982).

Sah, H., et al., "The Influence of Biodegradable Microcapsule Formulations on the Controlled Release of a Protein," *J. of Controlled Release* 30: 201–211 (1994).

COMPOSITION AND METHOD USING SOLID-PHASE PARTICLES FOR SUSTAINED IN VIVO RELEASE OF A BIOLOGICALLY ACTIVE AGENT

RELATED APPLICATION

This patent application claims priority to U.S. Provisional application Ser. No. 60/003,006, filed Aug. 31, 1995, the contents of which is incorporated herein by reference in its entirety.

BACKGROUND

Many illnesses or conditions require a sustained effective serum level of medicaments or agents in vivo to provide the most effective prophylactic, therapeutic or diagnostic results. In the past, single doses of medicaments typically resulted in insufficiently long periods of effective serum levels.

Attempts to control and sustain medication levels have more recently included the use of many biodegradable substances, such as poly(lactide) or poly(lactide-co-glycolide) microparticles containing the medicament. The use of these microparticles provided an improvement in the release characteristics of medicaments by utilizing the inherent biodegradability of polymers to improve the release of medicaments and to provide a more even, controlled level of medication. However, in some cases, the duration of release is limited by in vivo degradation properties of the polymer. Therefore, a need exists to exert additional control over in vivo release kinetics to provide longer periods of fairly consistent medicament serum levels in vivo.

SUMMARY OF THE INVENTION

The present invention relates to a composition for the sustained release of a biologically active agent in vivo. The composition comprises microcarriers containing a first solid-phase biocompatible material and a biologically active agent, wherein said microcarriers sustain the in vivo release of the biologically active agent. The composition also contains particles of a second biocompatible solid-phase material wherein the second solid-phase material further sustains the in vivo release of the biologically active agent.

The invention also relates to a method for sustaining effective serum levels of a biologically active agent in a subject, including forming a single dose containing an effective amount of a biologically active agent, wherein the agent is contained in a microcarrier, with a release-period sustaining amount of a solid-phase material. The method further includes administering the single dose to the subject.

This invention has the advantage of providing means for varying the periods for sustained release of biologically active agents over which an effective serum level of the biologically active agent will be maintained in vivo.

DETAILED DESCRIPTION OF THE INVENTION

A sustained release of a biologically active agent in vivo is a release which results in effective serum levels, typically above endogenouos levels, of the biologically active agent over a period longer than that obtained following direct administration of the biologically active agent in a physiologically acceptable carrier. An effective serum level of an agent is a level which results in the desired biological response within a subject.

A biologically active agent, as defined herein, is an agent, or its pharmaceutically acceptable salt, which possesses therapeutic, prophylactic or diagnostic properties in vivo. Examples of suitable therapeutic and/or prophylactic biologically active agents include, for instance, proteins such as immunoglobulin-like proteins, antibodies, cytokines (e.g., lymphokines, monokines, chemokines), interleukins, interferons, erythropoietin, nucleases, tumor necrosis factor, colony stimulating factors, insulin, enzymes, tumor suppressors, hormones (e.g., growth hormone and adrenocorticotrophic hormone), antigens (e.g., bacterial and viral antigens), growth factors; peptides; polypeptides; nucleic acids such as antisense molecules; and small molecules such as antibiotics, steroids, decongestants, neuroactive agents, anesthetics, sedatives, anti-tumor agents, cardiovascular agents, antineoplastics, antihistamines, hormones and vitamins.

Examples of suitable diagnostic and/or therapeutic biologically active agents include radioactive isotopes and radiopaque agents.

A microcarrier, as defined herein, comprises a particle having a diameter of about one millimeter to about one micrometer, or less, wherein the particle contains a biologically active agent and a first biocompatible solid-phase material, wherein the first solid-phase material sustains the in vivo release of the biologically active agent from the microcarrier. A microcarrier can have a spherical, non-spherical or irregular shape. The preferred microcarrier shape is generally spherical.

A biocompatible material, as defined herein, means that the material, and any degradation products of the material, are non-toxic to the recipient and also present no significant deleterious or untoward effects on the recipient's body, such as an immunological reaction at the injection site.

In one embodiment, the biologically active agent is encapsulated within a solid matrix formed of the biocompatible first solid-phase material. The biologically active agent, contained within the solid matrix, can be a solid, a liquid, in a suspension, in an emulsion or in a solution. Further, a biologically active agent, which is encapsulated within the solid matrix of a microcarrier, can be encapsulated as a single particle (or droplet) or preferably as at least two particles (or droplets) which are dispersed within the solid matrix of the microcarrier.

More preferably, the biologically active agent is in the form of particles that have been stabilized to prevent significant aggregation of the biologically active agent in vivo. Methods for stabilizing a biologically active agent against significant aggregation in vivo are further described in co-pending U.S. Continuation-in-Part patent application Ser. No. 08/521,744, filed on Aug. 31, 1995, now abandoned.

In the sustained release composition of the present invention, an effective amount of a biologically active agent is contained in a microcarrier. An effective amount of a biologically active agent is a therapeutically, prophylactically or diagnostically effective amount, which can be determined by a person of ordinary skill in the art taking into consideration factors such as species body weight; age; physical condition; therapeutic, prophylactic or diagnostic goal desired; type of agent used; type of substrate used; initial release and subsequent release levels desired; and release rate desired. Typically, a microcarrier for sustaining the release of a biologically active agent will contain from about 0.01% (w/w) biologically active agent to about 50k (w/w) biologically active agent, by weight.

Particles of a biologically active agent include, for example, crystalline particles, non-crystalline particles, freeze dried particles and lyophilized particles. The particles may contain only the biologically active agent or may also contain one or more stabilizing agents and/or other excipients.

Typically, the solid-phase material of the microcarrier is a biocompatible polymer which can be either a biodegradable polymer, a non-biodegradable polymer, blends thereof or copolymers thereof.

Biodegradable, as defined herein, means the polymer will degrade or erode in vivo to form smaller chemical species. Degradation can result, for example, by enzymatic, chemical and/or physical processes. Suitable biocompatible, biodegradable polymers include, for example, poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof.

Biocompatible, non-biodegradable polymers suitable for the modulated release composition of this invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Further, the terminal functionalities of a polymer can be modified. For example, polyesters can be blocked, unblocked or a blend of blocked and unblocked polymers. A blocked polyester is as classically defined in the art, specifically having blocked carboxyl end groups.

Generally, the blocking group is derived from the initiator of the polymerization and is typically an alkyl group. An unblocked polyester is as classically defined in the art, specifically having free carboxyl end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the PLGA used in the present invention has a molecular weight of about 5,000 Daltons to about 42,000 Daltons.

In an alternative embodiment, the biologically active agent is encapsulated in a lipid-based solid-phase material, such as waxes, or in a bioceramic material. Examples of suitable bioceramic materials include alumina, zirconium, calcium phosphate, calcium carbonate, zinc-calcium phosphorus oxide, zinc sulfate-calcium phosphate, ferric calcium phosphorus oxide, hydroxyapatite and aluminum oxide.

Particles of a biocompatible solid-phase material, suitable to further sustain the in vivo release of the biologically active agent, include particles of at least one biocompatible polymer, particles of at least one bioceramic material or particles of lipid-based materials. Preferably, the second solid-phase material particles are the same as, or similar to, the material comprising the first solid-phase material in the microcarriers.

In one embodiment the second solid-phase material particles also contain a biologically active agent which may be the same agent or a different agent than that contained in the microcarriers. When the second phase particles are the same materials as the material comprising the first solid-phase material, the biologically active agent may be the same or different, and if the same, may be formulated differently from the biologically active agent in the microcarriers.

In a preferred embodiment, at least a portion of the solid-phase material particles, when in vivo, agglomerate to form a body of the solid-phase material which further contains at least a portion of the microcarriers. A body of solid-phase material, as defined herein, typically means a solid or gel which is larger than the individual microcarriers and the individual solid-phase particles, and which is formed from individual solid-phase particles and microcarriers.

The period of sustained release of a biologically active agent is dependent upon the total mass of solid-phase material, contained in the microcarriers and the separate solid-phase particles, injected or implanted in a single dose at a single site in a subject. To further sustain the duration of in vivo release of a biologically active agent, the total mass of solid-phase material administered within a single dose, administered at a single site, must be at least at minimum mass. Wherein the total mass of solid-phase material administered in a single dose is the minimum mass or more, the period of release in vivo of the biologically active agent from the microcarriers will be significantly lengthened.

Usually, when the total mass of solid-phase material exceeds a maximum mass, no further increase in the duration of the sustained release period will occur and the release profile of the biologically active agent may be deleteriously affected. The minimum mass and maximum mass limit may vary depending on the type of biologically active agent, type of polymer, species of the subject and type of vehicle.

Typically, when the total mass of solid-phase material equals or exceeds the minimum mass, the initial burst level of biologically active agent is reduced, the time to obtain maximum serum level of biologically active agent is increased and the steady-state serum level of biologically active agent, late in the release period, is also increased.

Preferably, the total administered amount of solid-phase material is equal to or above the minimum mass limit and equal to or below the maximum mass limit.

In another preferred embodiment, the total mass of solid-phase material in a single dose is greater than the minimum mass and is sufficiently high to attain the desired loading of biologically active agent within the injectable dose.

The ratio of microcarriers to solid-phase particles, and the total overall size of a single dose, can be determined by a person of ordinary skill in the art by taking into consideration factors such as body weight; age; physical condition; therapeutic, prophylactic or diagnostic goal desired; type of agent used; initial burst and subsequent release levels desired; and release period desired.

In yet another embodiment, a sustained release composition of the present invention further contains a multivalent metal cation component for modulating the in vivo release of the biologically active agent.

A modulated release of a biologically active agent, as defined herein, is a release of a biologically active agent from a sustained release composition containing a multivalent metal cation component, wherein, at least one release characteristic, such as initial release level of said agent, subsequent agent release levels, the amount of agent released and/or the extent of the release period, is changed from the release characteristic(s) demonstrated for said biologically active agent sustained release composition not containing a multivalent metal cation component.

A multivalent metal cation component can be contained within the first biocompatible solid phase material and/or the particles of second solid-phase material.

A multivalent metal cation component, as defined herein, is a component containing at least one kind of metal cation, having a valence of +2 or more, in a non-dissociated state, a dissociated state, or a combination of non-dissociated and dissociated states. Suitable metal cation components include, for instance, metal salts, metal hydroxides, and basic (pH of about 7 or higher) salts of weak acids wherein the salt contains a metal cation. It is preferred that the metal cation be divalent.

In a preferred embodiment, wherein the first and second solid-phase materials are both biocompatible polymers, a suitable concentration of a multivalent metal cation component is dispersed within the polymer. A suitable concentration of a metal cation component is any concentration of a metal cation component which will modulate the release of a biologically active agent in vivo. Typically, a suitable proportion of a metal cation component is between about 1% (w/w) to about 30% (w/w). The optimum ratio depends upon the polymer, and upon the metal cation component and biologically active agent utilized. Preferably, a suitable amount of a metal cation component is between about 5% (w/w) to about 20% (w/w).

Examples of suitable sources of multivalent metal cations include, or contain, for example, magnesium hydroxide, magnesium carbonate, calcium carbonate, zinc carbonate, magnesium acetate, zinc acetate, magnesium sulfate, zinc sulfate, magnesium chloride, zinc chloride, zinc citrate, magnesium citrate and combinations thereof.

In a further embodiment, the sustained release composition of the present invention contains at least two different biologically active agents, for instance, two different proteins, such as erythropoietin and granulocyte-macrophage colony-stimulating factor. It is understood that each microcarrier can contain one or more types of biologically active agent. For example, a sustained release composition can contain different types of microcarriers, each containing different biologically active agents. Alternately, each microcarrier in the sustained release composition can contain all types of biologically active agent contained in the sustained release composition. Further, a sustained release composition can contain microcarriers having only one biologically active agent and also microcarriers containing more than one biologically active agent.

In an alternate embodiment, a sustained release composition of the present invention further comprises a physiologically acceptable vehicle, as are known to one of skill in the art, in which the microcarrier and the particles of solid-phase material are dispersed. Preferably, the vehicle is an aqueous solution.

In another preferred embodiment, the sustained release composition of the present invention contains only insignificant amounts of organic solvent, to typically prevent the occurrence of side effects associated with the in vivo administration of an organic solvent, such as tissue irritation at the injection site.

Microcarriers containing at least one biologically active agent, suitable for this invention, can be formed by any method known to one of skill in the art, such as by forming a matrix or reservoir using bioceramics or polymers; or by using emulsion techniques to form a microcarrier with lipid-based materials.

In one method for forming the microcarriers of the sustained release composition of the present invention, a suitable polymer is dissolved in a solvent to form a polymer solution. Examples of suitable solvents include, for instance, polar organic solvents such as methylene chloride, chloroform, tetrahydrofuran, dimethyl sulfoxide, hexafluoroisopropanol and ethyl acetate.

Typically, the polymer solution contains between about 5% to about 30% polymer by weight. More preferably, the polymer solution contains between about 5–15k polymer by weight. Biodegradable polymers are the preferred polymers for microcarriers with poly(lactide-co-glycolide) being the more preferred polymer.

At least one biologically active agent is mixed with the polymer solution. Preferably, the biologically active agent is in particulate form, or is in the aqueous component of an emulsion, and is not significantly soluble in the polymer solvent.

It is understood that the biologically active agent can be mixed with the polymer before the polymer is dissolved in the polymer solvent, while dissolving in the polymer solvent and/or after dissolving the polymer in the polymer solvent.

In one embodiment, a sustained release microcarrier is prepared by the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al., which are incorporated herein by reference.

In the solvent evaporation method, a polymer solution, which contains a biologically active agent, is mixed in or agitated with a continuous phase, in which the polymer's solvent is substantially immiscible, to form an emulsion. The continuous phase is usually an aqueous solvent. Emulsifiers are often included in the continuous phase to stabilize the emulsion. The polymer's solvent is then evaporated over a period of several hours or more, thereby solidifying the polymer to form a polymeric matrix containing a biologically active agent therein.

A preferred embodiment of a method for forming sustained release microcarriers from a polymer solution is described in U.S. Pat. No. 5,019,400, issued to Gombotz et al. and copending U.S. patent application Ser. No. 08/443,726, filed May 18, 1995, the teachings of which are incorporated herein in their entirety by reference. This method of polymeric microcarrier formation, as compared to other methods, such as phase separation, additionally reduces the amount of biologically active agent required to produce a sustained release microcarrier with a specific content of biologically active agent and also minimizes the loss of biological activity during microcarrier formation.

In this method the polymer solution, containing particles of biologically active agent, is processed to create droplets containing polymer solution and biologically active agent. These droplets are then frozen by means suitable to form polymeric microcarriers. Examples of means for processing the polymer solution dispersion to form droplets include directing the dispersion through an ultrasonic nozzle, pressure nozzle, Rayleigh jet, or by other means known for creating droplets from a solution.

Means suitable for freezing droplets to form microcarriers include directing the droplets into or near a liquified gas, such as liquid argon and liquid nitrogen to form frozen microdroplets which are then separated from the liquid gas. The frozen microdroplets are then exposed to a liquid non-solvent, such as ethanol, or ethanol mixed with hexane or pentane. The solvent in the frozen microdroplets is extracted as a solid and/or liquid into the non-solvent to form polymer microcarriers containing the biologically active agent. Mixing ethanol with other non-solvents, such as hexane or pentane, can increase the rate of solvent extraction above that achieved by ethanol alone from certain polymers, such as PLGA.

A wide range of sizes of microcarriers can be made by varying the droplet size, for example, by changing the ultrasonic nozzle diameter. The size of the microcarriers produced by this process can vary over a wide range, for example, from about one millimeter to about one micrometer, or less, in diameter.

The microcarriers are then mixed with particles of a biocompatible solid-phase material to form the sustained release composition of the present invention. Preferably, the solid-phase material particles are the same material, or a similar material, to the solid-phase material of the microcarrier. More preferably, each solid-phase material is a biocompatible, biodegradable polymer. Even more preferably, each solid-phase material is PLGA.

Suitable solid-phase particles include powders, particulates, and blank microparticles, which do not contain any biologically active agents and which can be formed by any method known in the art for forming microcarriers, such as microparticles, microcarriers and microcapsules. In a preferred embodiment, the solid-phase particles are formed as blank microcarriers by the method of co-pending U.S. patent application Ser. No. 08/443,726, filed May 18, 1995.

The particles of solid-phase material can have a wide variety of sizes. Typically, the diameters of the solid phase particles vary between about one millimeter and about one micrometer, or less.

In an alternate embodiment, the solid phase particles contain at least one biologically active agent, wherein the agent is the same agent as in the microcarrier, with a loading equal to or different from the loading in the microcarrier, and/or a different biologically active agent.

In a further embodiment, polymeric microcarriers and/or particles of solid-phase polymeric material are formed having a multivalent metal cation component disposed therein for modulating the release of the biologically active agent from the sustained release composition in vivo. A method for forming a composition for modulating the release of a biologically active agent from a biodegradable polymer is further described in co-pending U.S. patent application Ser. No. 08/237,057 now U.S. Pat. No. 5,656,297 and co-pending PCT Patent Application PCT/US95/05511.

In yet another embodiment, a sustained release composition of the present invention is formed by combining suitable microcarriers with particles of a solid-phase material within a physiologically acceptable vehicle wherein the total mass of solid-phase material, in the microcarriers and in the separate solid-phase particles, is equal to or greater than the minimum mass of the solid-phase material.

In the method for controlling the length of an in vivo release of a biologically active agent from a sustained release composition of this invention, the sustained release composition can be administered as a single dose at a single site to a human, or other animal, for example, by injection and/or implantation, subcutaneously, intramuscularly, intraperitoneally or intradermally to provide the desired dosage of a biologically active agent based on the known parameters for treatment of the various medical conditions with said agent.

In this method, the length of release, and the resultant serum levels, of at least one biologically active agent from the sustained release composition is affected by the choice of first solid-phase material used in forming the microcarrier and by the choice of solid-phase material particles used. The length of release is further affected by the amount of the first solid-phase material and/or second solid-phase material contained in a single dose of the sustained release composition administered at a single injection or implantation site.

A "release-period sustaining amount" of a solid phase material is the amount of a solid-phase material used to establish a specific sustained release period of biologically active agent in vivo for the sustained release composition of the present invention. For example, the periods over which effective serum levels of a biologically active agent are maintained, as shown in Examples 2 and 3 for human growth hormone (hGH), Example 5 for interferon (IFN), or Example 7 for erythropoietin (EPO) for single injections of the sustained release composition of the present invention, having about equal doses of biologically active agent, are a function of the amount of polymer contained in a single dose, with higher polymer amounts in a single dose resulting in significantly elongated periods of sustained, effective serum levels of the biologically active agent.

In another embodiment of the method for sustaining the in vivo release of a biologically active agent, the sustained release composition forms a mass in vivo which further sustains the release of the biologically active agent to produce an elongated period of effective serum levels of said agent. Suitable solid-phase materials to form a body in vivo include materials, in particle form, which under aqueous or physiologic conditions, will agglomerate or gel to form a body. This elongation of release period and serum levels is dependent upon the type and amount of solid-phase material used. For example, effective serum levels of biologically active agents are maintained significantly longer for a single dose of the sustained release composition of a present invention injected at one site than for half doses of the same sustained release composition injected concurrently at two different locations in the animal. See Examples 2, 3, 5 and 7 for further discussion of the injection dose size on sustaining effective serum levels.

The invention will now be further and specifically described by the following examples.

EXAMPLE 1

Formation of $Zn^{+2}$ Stabilized hGH Microcarriers

Purified recombinant human growth hormone, whose DNA sequence is described in U.S. Pat. No. 4,898,830, was used in this Example. The human growth hormone was stabilized by forming a complex with $Zn^{+2}$ ions, wherein the complex has a lower solubility in aqueous solutions than does non-complexed hGH.

The hGH was dissolved in a 4 mM sodium bicarbonate buffer (pH 7.2) to form an hGH solution with a concentration between 0.1 and 0.5 mM hGH. A 0.9 mM $Zn^{+2}$ solution was prepared from deionized water and zinc acetate dihydrate and then was added to the hGH solutions to form $Zn^{+2}$-hGH solution. The pH of the $Zn^{+2}$-hGH solution was then adjusted to between 7.0 and 7.4 by adding 1% acetic acid. A cloudy suspended precipitate, comprising $Zn^{+2}$-stabilized hGH formed.

The suspension of $Zn^{+2}$-stabilized hGH was then micronized using an ultrasonic nozzle (Type V1A; Sonics and Materials, Danbury, Conn.) and sprayed into a polypropylene tub (17 cm diameter and 8 cm deep) containing liquid nitrogen to form frozen particles. The polypropylene tub was then placed into a $-80°$ C. freezer until the liquid nitrogen evaporated. The frozen particles, which contained $Zn^{+2}$-stabilized hGH, were then lyophilized to form $Zn^{+2}$-stabilized hGH particles.

Microcarriers containing $Zn^{+2}$-stabilized hGH were then prepared from hydrophilic unblocked PLGA polymer (50:50 PLGA, 9,300 Daltons; RG502H polymer; Boehringer Ingelheim Chemicals, Inc., Montvale, N.J.).

The polymer was dissolved in methylene chloride (10 ml/gram PLGA) at room temperature to form a polymer solution. The lyophilized hGH particles were added to the polymer solution and zinc carbonate was also added. The mixture was then sonicated using an ultrasonic probe (Virtis Co., Gardiner, N.Y.) to give a homogeneous suspension. The suspension was atomized through a sonicating nozzle onto a bed of frozen ethanol, overlaid with liquid nitrogen. The vessel containing the microcarriers was stored at $-80°$ C. to extract the methylene chloride and the remaining particles were freeze-dried to give a free-flowing powder.

The encapsulation efficiency of the process was >90% because the suspension itself formed the final microcarriers and there were no emulsification processes. Any losses that occurred were due to transfer of the suspension between the sonicating vessel and the atomizing device. The absence of emulsification steps also avoided the use of surface-active stabilizers which may affect the release properties of the microcarriers.

EXAMPLE 2

Evaluation of the Effect of Microcarrier Polymer Mass on In Vivo Release of hGH in Rats The effect of microcarrier mass on the serum profile of hGH released from microcarrier formulations was evaluated in immunosuppressed rats.

Microcarriers of unblocked PLGA, containing 16% w/w $Zn^{+2}$-stabilized hGH (6:1 Zn Acetate:hGH) and 1% $ZnCO_3$ were formed by the method of Example 1. Male Sprague-Dawley rats (400±50 g) were injected subcutaneously in the mid scapular region with microcarriers suspended in injection vehicle (3% carboxymethyl cellulose (low viscosity) and 1% Tween 20 in 0.9k NaCl). The rats, which were divided into the following six treatment groups (N=3), were treated with hGH containing microcarriers on day 0 following anesthesia with Halothane.

| Group | Injection Type | Number of Injection Sites | Dose Per Injection Site |
| --- | --- | --- | --- |
| A | Single bolus | one | 50 mg hGH microcarriers in 1 ml of vehicle |
| B | Single bolus | one | 100 mg hGH microcarriers in 1 ml of vehicle |
| C | Single bolus | one | 360 mg hGH microcarriers in 3 ml of vehicle |
| D | Single bolus | two | 25 mg hGH microcarriers in 1 ml of vehicle |
| E | Single bolus | two | 50 mg hGH microcarriers in 1 ml of vehicle |
| F | Single bolus | two | 150 mg hGH microcarriers in 1 ml of vehicle |

To suppress their immune systems, the rats were treated with 10 mg/kg cyclosporin A (Sandimmune® Injection, Sandoz, East Hanover, N.J.) and 5 mg/kg hydrocortisone (Spectrum Co., Gardena, Calif.) in 0.5 ml sterilized saline for injection (USP) delivered intraperitoneally for days 0–14 (except for Sundays) and three times weekly for days 15–42.

Blood samples (at least 2501 for timepoints in the first 24 hours and at least 4001 for timepoints after 24 hours) were collected via a lateral tail vein, after anesthesia with Halothane, at day 0 before treatment with the hGH-containing microcarriers and after treatment at 2, 4, 6, 10, and 24 hours, and at 2, 3, 5, 6, 7, 9, 12, 15, 19, 22, 26, 29, and 33 days post-treatment. Each blood sample was transferred to a blood serum separator tube (Capiject®; Terumo Medical Corp.; Elkton, Md.). The blood was allowed to clot for 30 minutes at room temperature, then centrifuged (1200×G or 3600 rpm; micro-centrifuge Model 235C, Fisher Scientific, Bohemia, N.Y.) for 5 minutes at 4° C. and stored at −80° C. hGH concentrations in serum were determined using a radio-immunoassay kit (RIA) purchased from ICN Biomedical (Los Angeles, Calif.). The release profiles are shown in FIGS. 1 through 3.

Figure 1:
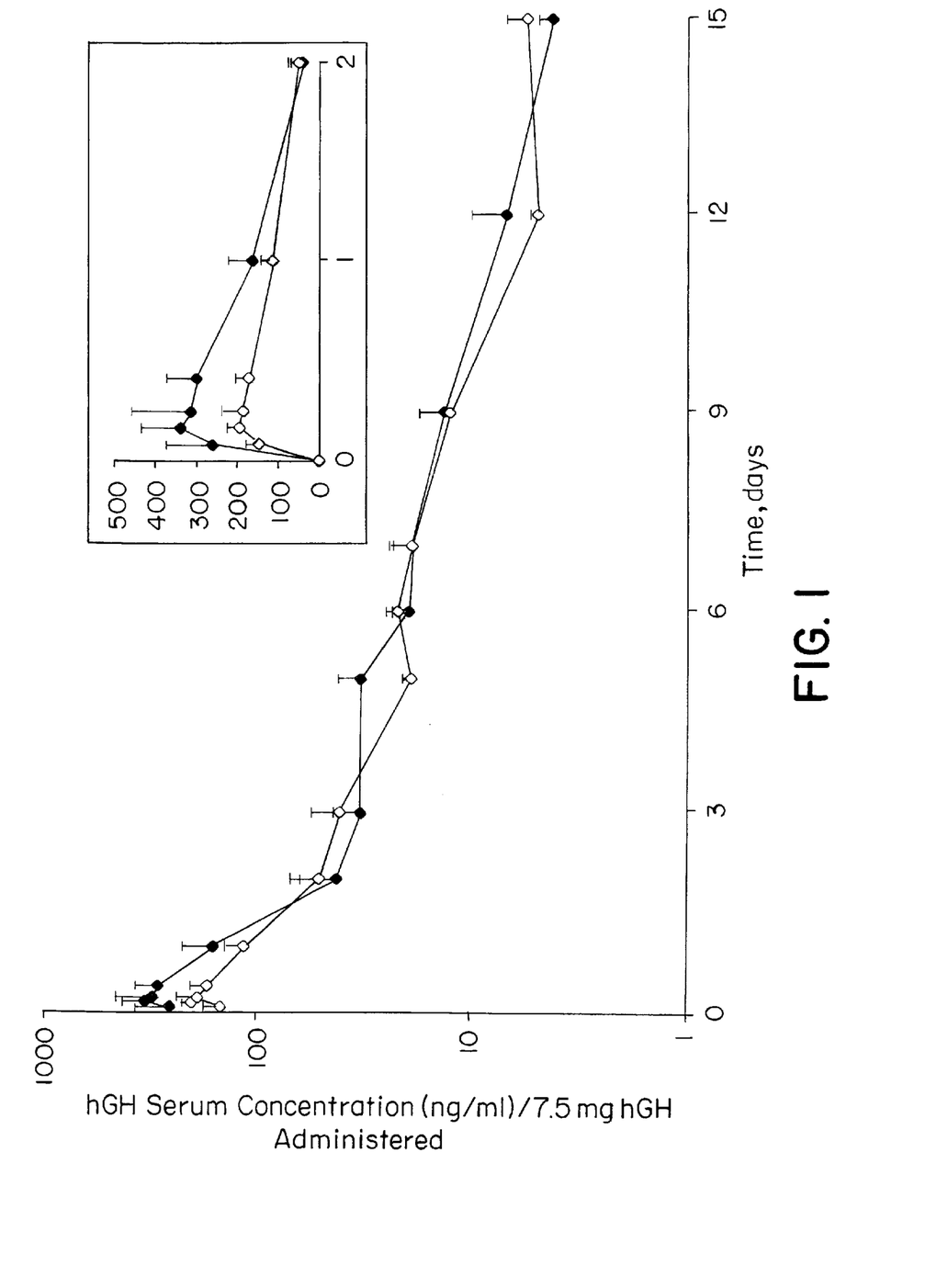
FIG. 1 is a plot of the average serum concentration (ng/ml) of human growth hormone (hGH) in immunosuppressed rats which were subcutaneously injected with a 50 mg dose of hGH-containing microcarriers administered as a) one 50 mg injection (filled diamonds) or b) two 25 mg injections (open diamonds) at two separate sites in each rat, versus time over a 15 day interval.

Comparison of the serum profiles of rats in groups A and D, shown in FIG. 1, suggest that at the 50 mg hGH microcarrier dose, administered as one or two injections, an extended constant release phase was not observed although serum levels were elevated above baseline for 15 to 18 days and the serum hGH concentrations had returned to baseline by 18 days.

Figure 2:
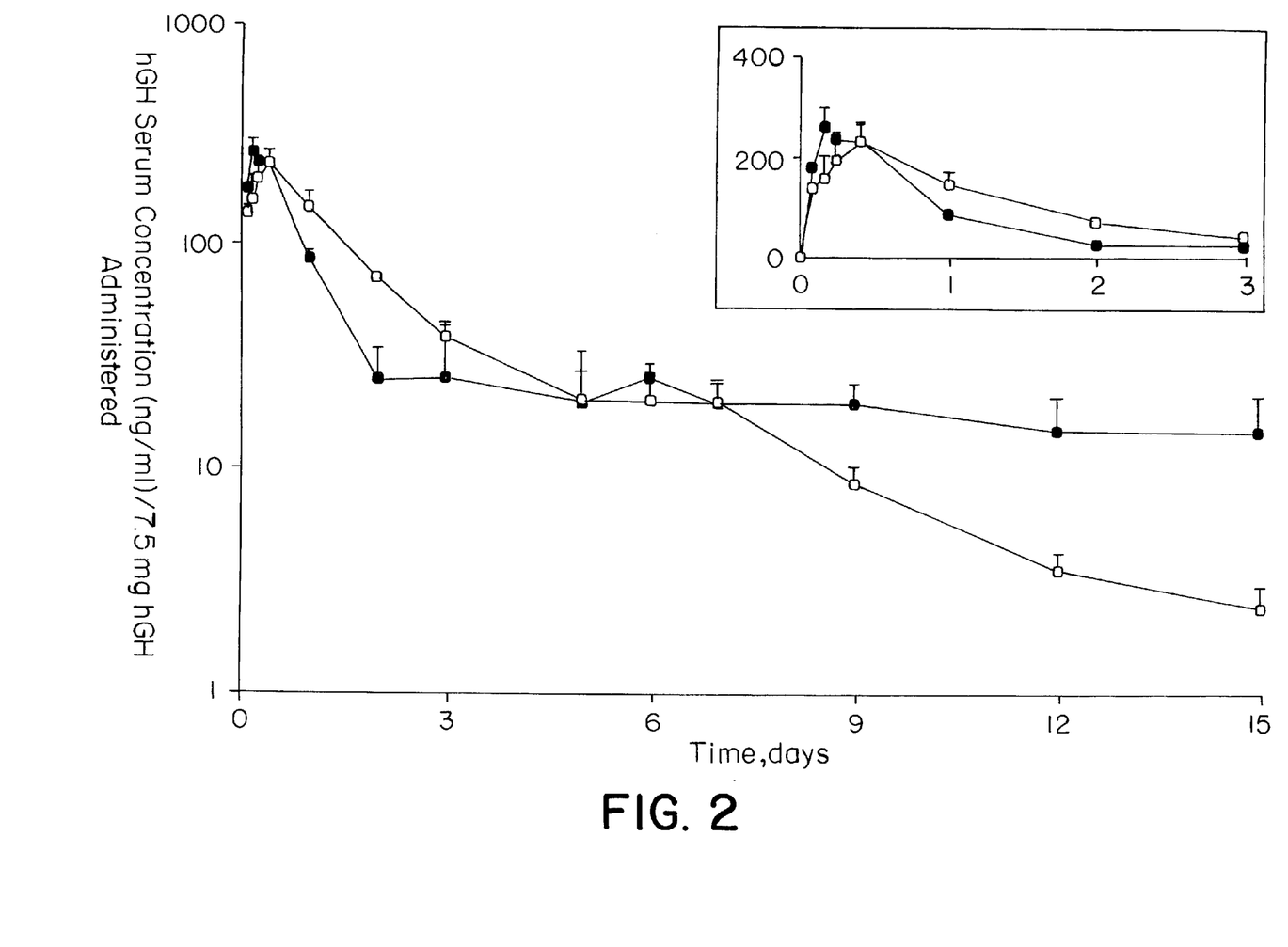
FIG. 2 is a plot of the average serum concentration (ng/ml) of hGH in immunosuppressed rats which were subcutaneously injected with a 100 mg dose of hGH-containing microcarriers administered as a) one 100 mg injection (filled squares) or b) two 50 mg injections (open squares) at two separate sites in each rat, versus time over a 15 day interval.

Comparison of the serum profiles from groups B and E, shown in FIG. 2, show a significant difference in serum hGH concentrations observed for Group B and for Group E. For Group E, wherein the 100 mg dose of microcarriers was administered as two equivalent subcutaneous injections at two different injection sites, serum hGH concentrations returned to baseline at 19 days without a significant phase of constant, sustained hGH release. However, when the same hGH microcarrier dose was administered as a single subcutaneous injection in Group B, hGH serum levels remained at a constant, elevated level from days 2 through 15. The hGH serum levels then returned to baseline at 22 days.

Figure 3:
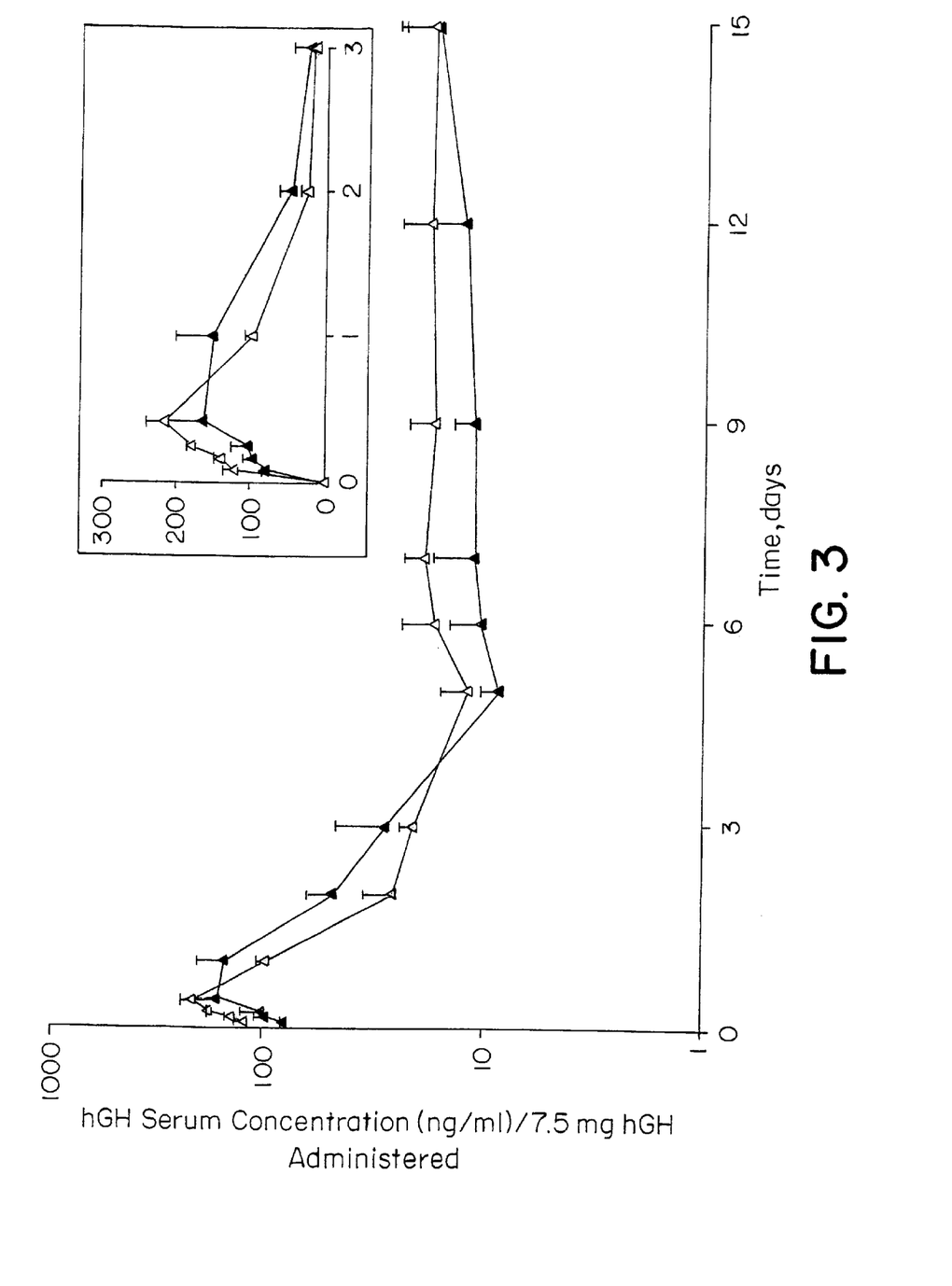
FIG. 3 is a plot of the average serum concentration (ng/ml) of hGH in immunosuppressed rats which were subcutaneously injected with a 300 mg dose of hGH-containing microcarriers administered as a) one 300 mg injection (filled triangles) or b) two 150 mg injections (open triangles) two separate sites in each rat, versus time over a 15 day interval.

However, a comparison shown in FIG. 3, of the hGH serum profiles of animals in groups C and F, which received 300 mg of microcarriers either as a single injection or two injections of 150 mg, showed no significant differences. In each group, there was a constant release phase between days 5 and 16 and the serum hGH concentrations returned to baseline at 22 days.

For this formulation of hGH-containing microcarriers, injected in rats, the results provided in FIGS. 1 and 2 suggest that the minimum mass of polymeric solid-phase material in the microcarriers, above which a constant sustained release of hGH in vivo is achieved, is contained in a single injected dose containing more than 50 mg of microcarriers and up to 100 mg of microcarriers. When this minimum mass was exceeded as shown in FIGS. 2 and 3 (Groups B, C and F) the constant release phase was observed. In addition, their serum hGH levels were elevated above baseline for an additional 3 days in these groups compared to the other groups.

Furthermore, the results provided in FIGS. 2 and 3 indicate that the maximum mass for polymeric solid-phase material, above which no additional effect on sustained release occurs, is contained in a single injected dose containing more than 100 mg of microcarriers and up to 150 mg of microcarriers.

EXAMPLE 3

Evaluation of the Effect of Additional Polymer Mass on In Vivo Release of hGH hGH microcarriers were formulated as described in Example 1. Blank microcarriers lacking $Zn^{+2}$-stabilized hGH, but containing 1% $ZnCO_3$ were also prepared by the method described in Example 1.

Male Sprague-Dawley rats were immunosuppressed with cyclosporin A and hydrocortisone as described in Example 2. The rats were divided into five treatment groups (N=3), which were administered the formulations as follows, using method described in Example 2.

| Group | Injection Type | Number of Injection Sites | Dose Per Injection Site |
|---|---|---|---|
| A | Single bolus | one | 50 mg hGH microcarriers + 50 mg blanks in 1 ml of vehicle |
| B | Single bolus | two | 25 mg hGH microcarriers + 25 mg blanks in 1 ml of vehicle |
| C | Single bolus | one | 50 mg hGH microcarriers + 150 mg blanks in 1 ml of vehicle |
| D | Single bolus | two | 25 mg hGH microcarriers + 75 mg blanks in 1 ml of vehicle |

Figure 4:
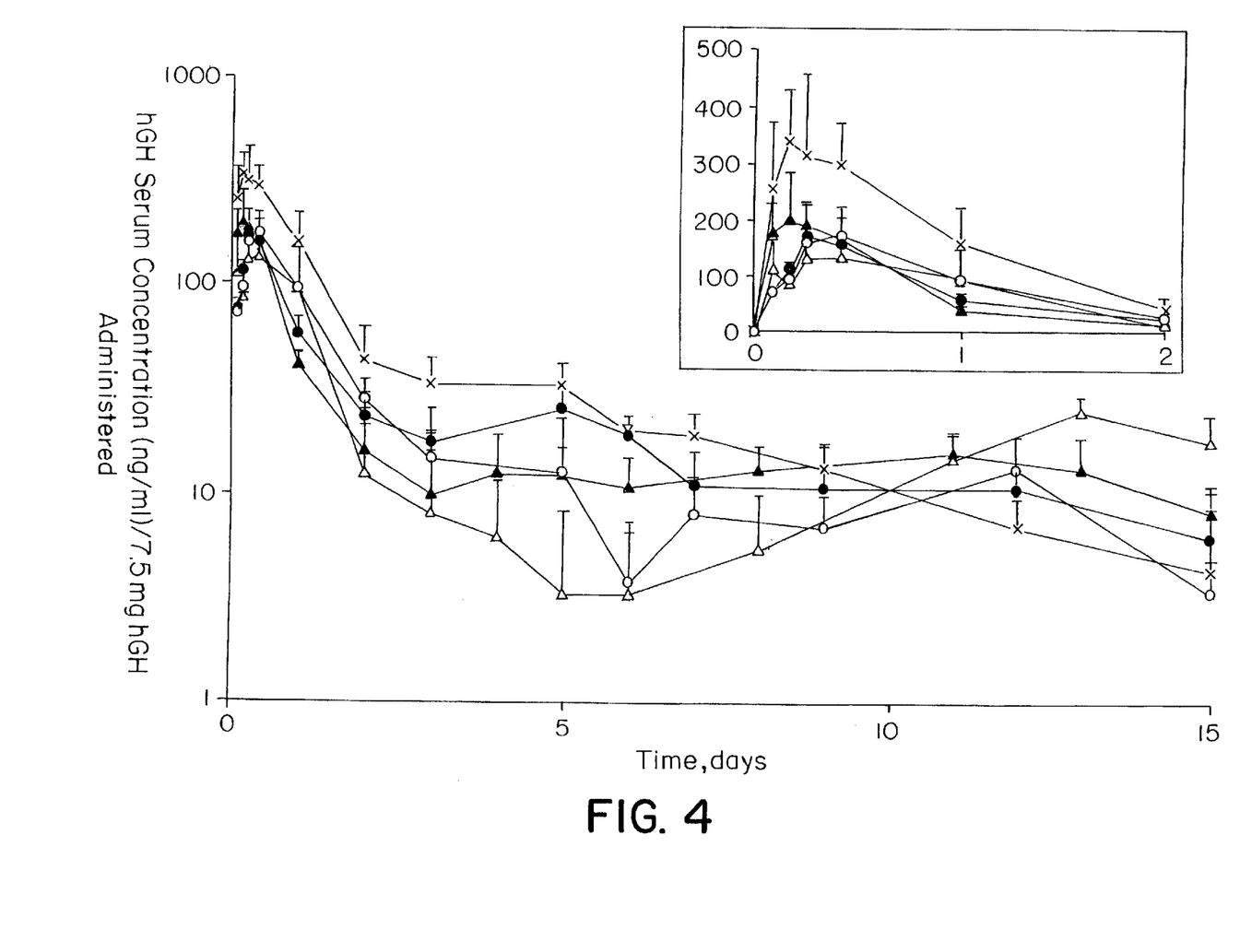
FIG. 4 is a plot of the average serum concentration (ng/ml) of hGH in immunosuppressed rats which were subcutaneously administered a) one injection of 50 mg of hGH microcarriers (X), b) one injection of 50 mg of hGH microcarriers and 50 mg of blank microcarriers (filled triangles), c) one injection of 50 mg of hGH microcarriers and 150 mg of blank microcarriers (open triangles), d) two separate injections each of 25 mg of hGH microcarriers and 25 mg of blank microcarriers (filled circles), and e) two separate injections each of 25 mg of hGH microcarriers and 75 mg of blank microcarriers (open circles), versus time over a 15 day interval.
Figure 5:
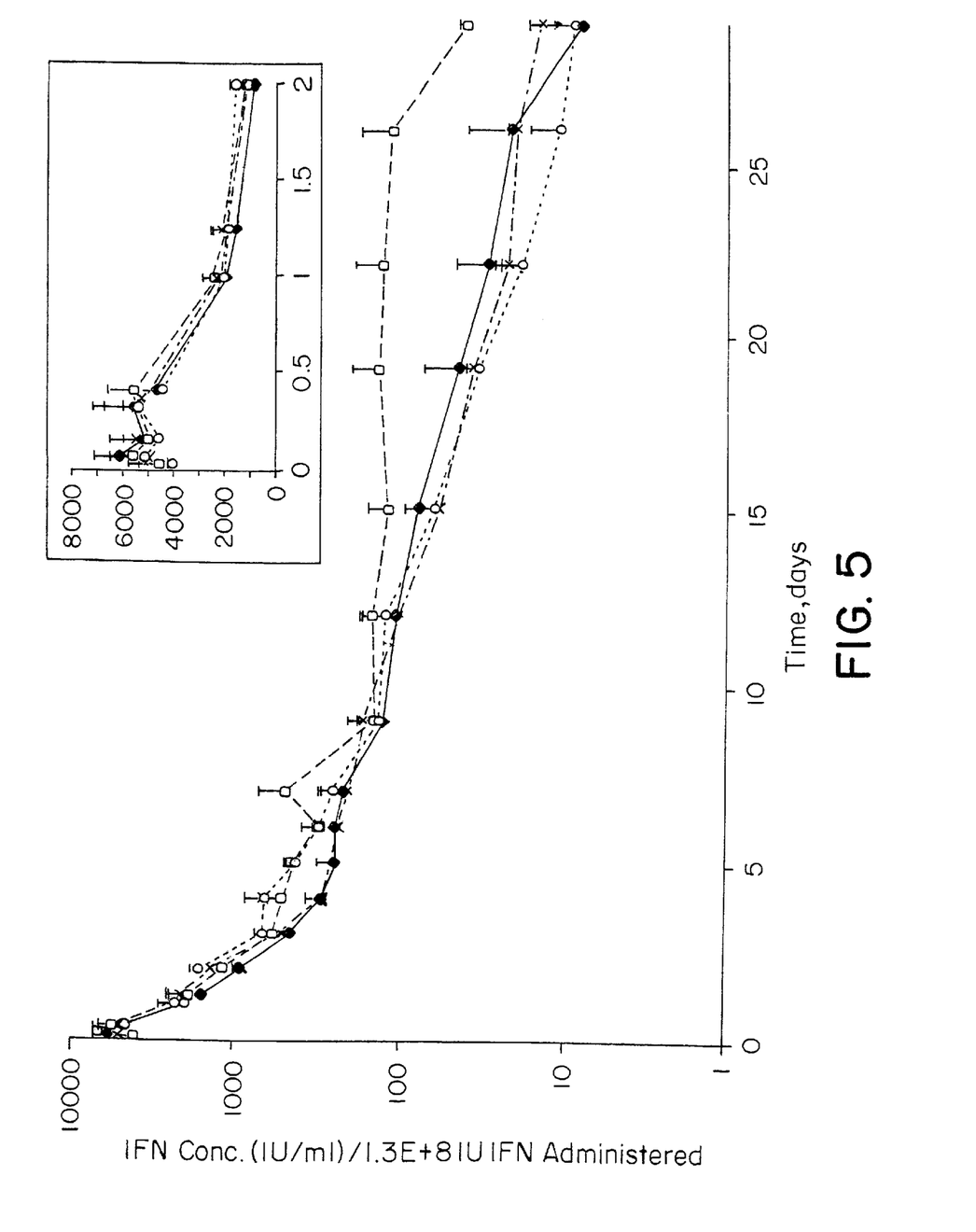
FIG. 5 is a plot of the average serum concentration (IU/ml) of interferon-$\alpha$ (IFN-$\alpha$) in immunosuppressed rats which were subcutaneously injected with IFN-containing microcarriers administered in a) one 10 mg injection (filled diamonds), b) one 20 mg injection (open squares), c) two 10 mg injections (open circles) administered at two separate sites in each rat, or (d) one injection of 10 mg IFN-60 microcarriers and 10 mg of blank polymeric microcarriers (X) versus time over a 29 day interval.

Blood samples were collected prior to injection of the microcarriers and at 2, 4, 6, 10 and 24 hours, and 2, 3, 4, 5, 6, 8, 11, 13, 15, 19, 22, 26, 29 and 33 days post-treatment. The hGH serum concentrations were then analyzed by JRMA for each blood sample as described in Example 2. The results of these analyses are provided in FIG. 4 as compared to the Group A rats of Example 2 which constitutes a control group. These results show that the rats receiving additional polymeric solid-phase material as blank microcarriers in single injections, sustained higher hGH serum levels at the end of the release period than did the rats who received split doses injected at two sites.

EXAMPLE 4

Formation of $Zn^{+2}$-Stabilized Interferon Microcarriers

IFN-α,2b, which was used in the present Example, is identical to IFN-α,2 as described in Rubenstein et al., *Biochem. Biophys. Acta*, 695: 705–716 (1982), with the exception that the lysine at position 23 of IFN-α,2 is an arginine in IFN-α,2b. The IFN-α,2b was dissolved in 10 mM sodium bicarbonate buffer (pH 7.2) to form an IFN solution with a concentration between 0.1 and 0.5 mM IFN. A 10 mM $Zn^{+2}$ solution was prepared from deionized water and zinc acetate dihydrate and then was added to the IFN solution to form a $Zn^{+2}$-IFN solution with a final IFN concentration of about 1.3 mg/ml and a $Zn^{+2}$:IFN molar ratio of 2:1. The pH of the $Zn^{+2}$-IFN solution was then adjusted to 7.1 by adding 1% acetic acid. A cloudy suspended precipitate, comprising $Zn^{+2}$-stabilized IFN, formed in the solution.

As described in Example 1, the suspension of $Zn^{+2}$-stabilized IFN was then micronized using an ultrasonic nozzle and sprayed into a polypropylene tub containing liquid nitrogen to form frozen particles. The polypropylene tub was then placed into a −80° C. freezer until the liquid nitrogen evaporated. The frozen particles, which contained $Zn^{+2}$-stabilized IFN, were then lyophilized to form $Zn^{+2}$-stabilized IFN particles.

An IFN microcarrier formulation having a mass ratio of zinc carbonate to IFN of 1:1 was then prepared. Blocked PLGA (0.41 g) (intrinsic viscosity of 0.15 dl/g; Birmingham Polymers, Birmingham, Ala.) was dissolved in 4.1 ml of methylene chloride to form a polymer solution. To this polymer solution was added 40 mg of lyophilized $Zn+^2$-stabilized IFN particles, containing 2 moles of zinc ions per mole of IFN and about 10.0 mg of sodium bicarbonate. Additionally, 50 mg of zinc carbonate was added to the polymer solution.

The polymer solution and $Zn^{+2}$-stabilized IFN particles were then sonicated using an ultrasonic probe to fragment and suspend $Zn^{+2}$-stabilized IFN particles in the polymer solution. The size of the sonicated, $Zn^{+2}$-stabilized IFN particles was between 2–6 microns. The IFN suspension was then placed in a 10 ml gas-tight syringe.

A 164 ml volume of 100% ethanol was added to the round polypropylene tub. This solution was frozen by surrounding the tub with liquid nitrogen. The frozen ethanol was then covered with 500 ml of liquid nitrogen. The IFN suspension was then pumped from the syringe by a syringe pump (Orion Sage Pump Model 355, Orion Research Inc., Boston, Mass.), at a rate of 1.7 ml/min, into an ultrasonic nozzle (Type V1A, Sonics and Materials, Danbury, Conn.) that was placed above the container containing the frozen ethanol covered with liquid nitrogen. The nozzle atomized the IFN suspension into droplets which froze upon contact with the liquid nitrogen and formed microcarriers which sank to the surface of the frozen ethanol.

The container was placed into a −80° C. freezer, thereby evaporating the liquid nitrogen and allowing the ethanol to melt. As the ethanol thawed, the microcarriers sank into it. The temperature was lowered to −95.1° C. and the methylene chloride was extracted from the microcarriers. After 24 hours, an additional 164 ml of 100% ethanol, which was prechilled to −80° C., was added to the container. Three days after the microcarriers were prepared, the ethanol/microcarrier slurry was filtered using a 0.65 micron Durapore™ membrane (Millipore, Bedford, Mass.). The filtered microcarriers were then vacuum dried in a lyophilizer.

EXAMPLE 5

Evaluation of the Effect of Polymer Mass on In Vivo Release of IFN in Rats

Four groups of male Sprague-Dawley rats (N=3) were immunosuppressed using cyclosporin A and hydrocortisone, as described in Example 2, and then were injected with IFN-containing microcarriers of Example 4 on day 0 as follows:

| Group | Injection Type | Number of Injection Sites | Dose Per Injection Site |
|---|---|---|---|
| A | Single bolus | one | 20 mg IFN microcarriers in 0.75 ml of vehicle |
| B | Single bolus | one | 10 mg IFN microcarriers in 0.75 ml of vehicle |
| C | Single bolus | two | 10 mg IFN microcarriers in 0.75 ml of vehicle |
| D | Single bolus | one | 10 mg IFN microcarriers and 10 mg of blank polymeric microcarriers containing zinc carbonate in 0.75 ml of vehicle |

Serum levels of IFN were determined by immunoradiometric assay (IRMA) through day 29. These results are provided in FIG. 5. At the 29 day timepoint, the serum IFN concentration in Groups B and C rats were at the minimum limit of detection for the assay, however, the serum IFN concentration in Group A rats, at this timepoint, was approximately 5-fold higher demonstrating a sustained release dose to the higher mass of polymeric solid-phase material injected at a single site in the Group A rats.

EXAMPLE 6

Formation of Aggregation-Stabilized EPO Microcarriers

Erythropoietin (EPO) was derived as described in U.S. Pat. No. 4,703,008. The EPO was dissolved in deionized water to form an aqueous solution having a concentration of approximately 1 mg/ml. The EPO solution were then dialyzed against three changes of a 5 mM phosphate buffer (pH 7) formulation buffer.

Following dialysis, the concentration of EPO in the dialyzed solution was verified to be approximately 1 mg/ml as determined by measuring absorbance at 280 nm ($\epsilon$=1.345 L $gm^{-1}$ $cm^{-1}$).

The dialyzed EPO solution was then mixed by gentle inversion with concentrated solutions of ammonium sulfate and inulin in a 50 ml polyproplene tube to form an aggregation-stabilized EPO formulation containing, in weight percent, 9.9% EPO, 79.1 ammonium sulfate, 10k phosphate buffer and 1.0% inulin.

The ammonium sulfate/inulin solution previously was prepared, separately, in 5 mm phosphate buffer (pH7).

Lyophilized, aggregation-stabilized EPO particles were then formed from the EPO solution by the method described in Example 1. The EPO particles were removed from the lyophilizer under an atmosphere of dry nitrogen, handled in a low humidity environment, and stored desiccated at −80° C.

Microcarriers containing the aggregation-stabilized EPO were then prepared, also using the method of Example 1 from hydrophilic unblocked PLGA polymer (50:50 PLGA; MW 9,300 Daltons, from Boehringer Ingelheim Chemicals, Inc., Montvale, N.J.). The polymer was dissolved in 5.1 ml of methylene chloride to form a polymer solution. Magnesium carbonate was sieved through a 38 micrometer sieve and was then added to the polymer solution to a final concentration of 10% w/vol. The polymer/salt suspension was subsequently combined with 30 mg of aggregation-stabilized EPO particles.

The polymer solution, containing suspended salt and EPO particles, was placed in an ice-water bath and sonicated using an ultrasonic probe (Virtis Co., Gardiner, N.Y.) to reduce the protein particle size to approximately 2 to 3 micrometers in diameter and to form a dispersion of EPO particles within the polymer solution.

A frozen bed of ethanol was prepared in a polypropylene tub by surrounding the tub with liquid nitrogen, then covering the frozen ethanol with additional liquid nitrogen. The EPO/polymer suspension was then pumped at a rate of 1–2 ml/min from a syringe by a syringe pump (Orion Research Inc., Boston, Mass.) into an ultrasonic nozzle placed above the container of frozen ethanol and liquid nitrogen. The EPO/polymer suspension was atomized into droplets which froze upon contact with the liquid nitrogen and formed microcarriers which sank to the surface to the frozen ethanol.

The container was placed at −80° C. to evaporate the liquid nitrogen and allow the ethanol to melt. As the ethanol thawed, the microcarriers sank into the ethanol and the methylene chloride was extracted from the microcarriers. After 24 hours, additional ethanol, which was prechilled to −80° C., was added to the container. Two days after the microcarriers were prepared, the ethanol/microcarrier slurry was filtered through a 0.65 micron Durapure® membrane (Millipore, Bedford, Mass.) using a precooled filter apparatus. The filtration was performed in a glove box that was preflushed with nitrogen gas. The filtered microcarriers were then lyophilized (on a shelf that had been precooled to −40° C.) until dry.

EXAMPLE 7

Evaluation of the Effect of Polymeric Microcarrier Mass on In Vivo Release of EPO in Rats The effect of microcarrier mass on the serum profile of EPO released from microcarrier formulation of Example 6 was evaluated in rats which were immunosuppressed as described in Example 2.

The rats were divided into three treatment groups (N=3), and were administered the EPO-containing microcarriers of Example 6 using the method described in Example 2, as follows:

| Group | Injection Type | Number of Injection Sites | Dose Per Injection Site |
|---|---|---|---|
| A | Single bolus | one | 20 mg EPO microcarriers in 0.75 ml of vehicle |
| B | Single bolus | two | 40 mg EPO microcarriers in 0.75 ml of vehicle |
| C | Single bolus | four | 5 mg EPO microcarriers in 0.19 ml of vehicle |

The microcarriers were suspended in an injection vehicle containing 1% glycerol, 0.9% NaCl, 0.5% gelatin and 2% CMC (LV).

Figure 6:
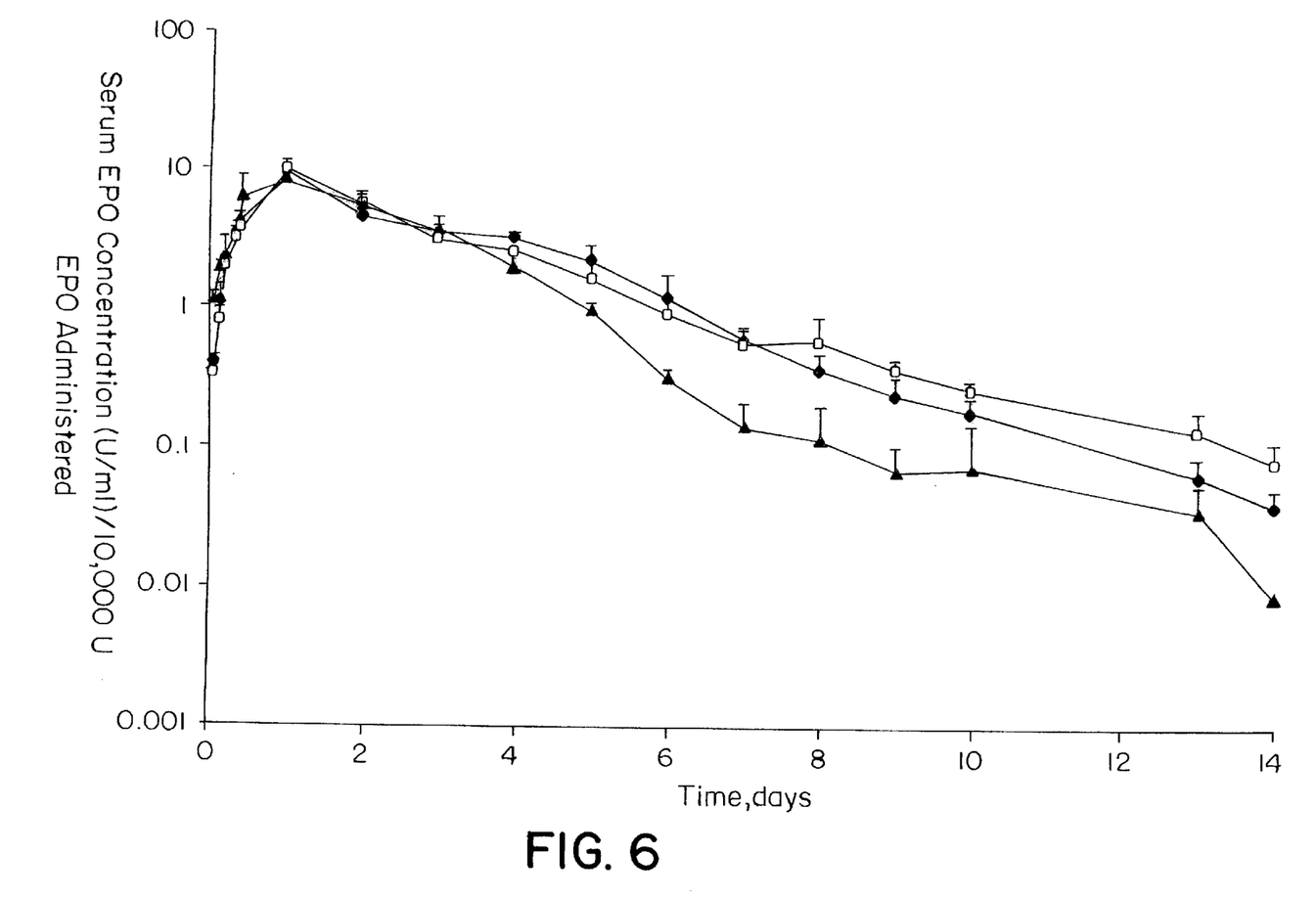
FIG. 6 is a plot of the average serum concentration (U/ml) of erythropoietin (EPO) in immunosuppressed rats which were subcutaneously injected with a) a single injection of 20 mg of EPO-containing microcarriers (filled diamonds), b) a single injection of 40 mg of EPO-containing microcarriers (open squares) and c) four separate injections each of 5 mg of EPO-containing microcarriers (filled triangles), versus time over a 14 day interval.

Blood samples (400 μl) were collected via a lateral tail vein after anesthesia with Halothane before treatment with microcarriers and at 1, 3, 5, 8, 10 and 24 hours, and 2, 3, 4, 5, 6, 7, 8, 9, 10, 13 and 14 days post-treatment. Each blood sample was transferred to a blood serum separator tube (Microtainer®; Becton Dickinson, Item #BD5960). The blood was allowed to clot for 30 minutes at room temperature, then centrifuged (1,200×G or 3,600 rpm; micro-centrifuge Model 235C, Fisher Scientific, Bohemia, N.Y.) for 15 minutes at 4° C. and stored at −80° C. The EPO concentrations in serum were determined using a commercially available ELISA kit according to manufacturer's instructions (Quantitative IVD, R&D Systems, Minneapolis, Minn.). The EPO release profiles, shown in FIG. 6, also exhibit the sustained release effect of increased mass of polymeric solid-phase material administered in a single dose.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

The invention claimed is:

1. A pharmaceutical composition for the sustained release in vivo of a biologically active agent, comprising:
    a) microcarrier particles of about one millimeter or less containing an effective amount of a biologically active agent encapsulated within a first polymer which biocompatible and selected from the group consisting of poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof, wherein the microcarriers sustain the in vivo release of the biologically active agent, and
    b) microparticles of about one millimeter or less of a second polymer which is biocompatible and biodegradable, wherein said microparticles are substantially free of the biologically active agent, and which are separate form but commingled with the microcarrier particles of a) and are present in an amount sufficient to elongate the release period of biologically active agent from the microcarrier particles of a).

2. A sustained release composition of claim 1 wherein the first polymer and the second polymer are the same polymer.

3. A sustained release composition of claim 1 wherein the first polymer is a different polymer than the second polymer.

4. A sustained release composition of claim 1 wherein the second polymer is selected from the group consisting of poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof.

5. A sustained release composition of claim 1 wherein the biologically active agent is a protein.

6. A sustained release composition of claim 1 further comprising a physiologically acceptable vehicle.

7. A sustained release composition of claim 1 wherein the first polymer further contains at least one multivalent metal cation component for modulating the release of the biologically active agent in vivo.

8. A sustained release composition of claim 1 wherein the second polymer further contains at least one multivalent metal cation component for modulating the release of the biologically active agent in vivo.

9. A sustained release composition of claim 1 wherein the first polymer is poly(lactide-co-glycolide).

10. A method for the sustained release in vivo of a biologically active agent comprising administering to a subject an effective amount of a sustained release composition comprising:
    a) microcarrier particles of about one millimeter or less containing a biologically active agent encapsulated within a first polymer which is biocompatible and selected from the group consisting of poly(lactide)s, poly(glycolide)s, poly(lactide-co-glycolide)s, poly)lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof, wherein the microcarrier particles sustain the in vivo release of the biologically active agent,
    b) microparticles of a second polymer which is biocompatible and biodegradable, wherein said microparticles are substantially free of the biologically active agent, and which are separate from but commingled with the microcarrier particles of a) and are present in an amount sufficient to elongate the release period of biologically active agent from the microcarrier particles of a), and
    a physiologically acceptable vehicle.

11. The sustained release composition of claim 5 wherein the protein is aggregation-stabilized.

12. A method of claim 10 wherein the first polymer is poly(lactide-co-glycolide).

13. A method of claim 10 wherein the first polymer is a different polymer that the second polymer.

14. A method of claim 10 wherein the second polymer is selected from the group consisting of poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, blends and copolymers thereof.

15. A method of claim 10 wherein the biologically active agent is a protein.

16. A method of claim 15 wherein the protein is aggregation-stabilized.

17. A method of claim 10 wherein the first polymer further contains at least one multivalent metal cation component for modulating the release of the biologically active agent in vivo.

18. A method of claim 10 wherein the second polymer further contains at least one multivalent metal cation component for modulating the release of the biologically active agent in vivo.

* * * * *